US006869653B2

(12) United States Patent
Ling et al.

(10) Patent No.: US 6,869,653 B2
(45) Date of Patent: Mar. 22, 2005

(54) PORT TUBE CLOSURE ASSEMBLY

(75) Inventors: Michael T. K. Ling, Vernon Hills, IL (US); William S. Hurst, Burlington, WI (US); Lecon Woo, Libertyville, IL (US); Algirdas Bindokas, Clarendon Hills, IL (US); Patrick T. Ryan, Crystal Lake, IL (US); Scott D. Edwards, Libertyville, IL (US); Henk P. Blom, Mundelein, IL (US); Atul R. Khare, Crystal Lake, IL (US)

(73) Assignee: Baxter International Inc., Dearfield, IL (US)

( * ) Notice: Subject to any disclaimer, the term of this patent is extended or adjusted under 35 U.S.C. 154(b) by 0 days.

(21) Appl. No.: 09/756,490

(22) Filed: Jan. 8, 2001

(65) Prior Publication Data

US 2002/0090476 A1 Jul. 11, 2002

(51) Int. Cl.[7] .............................................. C08L 47/00
(52) U.S. Cl. ................... 428/36.9; 428/476.1; 428/516; 428/519; 428/521
(58) Field of Search .......................... 428/35.7, 36.9, 428/476.1, 516, 519, 521

(56) References Cited

U.S. PATENT DOCUMENTS

| 2,324,237 | A | 7/1943 | Reichel .................... 215/32 |
| 2,342,215 | A | 2/1944 | Perelson .................. 215/38 |
| 2,562,389 | A | 7/1951 | Piazze ..................... 229/62 |
| 2,808,829 | A | 10/1957 | Butler .................... 128/272 |
| 2,894,510 | A | 7/1959 | Bellamy .................. 128/272 |
| 2,940,444 | A | 6/1960 | Beall ..................... 128/214 |
| 3,030,952 | A | 4/1962 | Elder ..................... 128/214 |
| 3,161,310 | A | 12/1964 | Barton et al. ............... 215/1 |
| 3,442,737 | A | 5/1969 | Reed et al. ............... 156/158 |
| 3,514,359 | A | 5/1970 | Frese .................... 156/308 |
| 3,589,422 | A | 6/1971 | Bellamy et al. ............. 150/1 |
| 3,642,047 | A | 2/1972 | Waage ..................... 150/8 |
| 3,746,001 | A | 7/1973 | Ralston, Jr. ............... 128/214 |
| 3,769,136 | A | 10/1973 | Ospelt .................... 156/308 |
| 3,788,374 | A | 1/1974 | Saijo ...................... 150/1 |
| 3,861,973 | A | 1/1975 | Koch ...................... 156/143 |
| 3,866,631 | A | 2/1975 | Chudgar ................... 138/125 |
| 3,869,338 | A | 3/1975 | Kavesh .................... 161/165 |
| 3,900,640 | A | 8/1975 | Vecchiotti ................. 428/36 |
| 3,911,051 | A | 10/1975 | Schouten et al. .......... 260/876 B |
| 3,928,110 | A | 12/1975 | Arconti et al. ............. 156/308 |
| 3,951,148 | A | 4/1976 | Herb ..................... 128/272 |
| 3,963,026 | A | 6/1976 | Herb ..................... 128/272 |
| 3,978,859 | A | 9/1976 | Goodenough et al. ....... 128/272 |
| 3,986,507 | A | 10/1976 | Watt .................... 128/214 D |
| 3,991,912 | A | 11/1976 | Soto ..................... 222/89 |
| 4,049,034 | A | 9/1977 | Vcelka et al. .............. 150/8 |
| 4,137,117 | A | 1/1979 | Jones .................... 156/294 |

(List continued on next page.)

FOREIGN PATENT DOCUMENTS

| EP | 0564231 B1 | 10/1993 |
| EP | 0623651 B1 | 11/1994 |
| EP | 0765740 A3 | 4/1997 |
| EP | 1059479 A1 | 12/2000 |
| WO | WO 95/13918 | * 5/1995 |

OTHER PUBLICATIONS

PCT Appl PCT/US 02/00299 Written Opinion mailed May 21, 2003.

Primary Examiner—Sandra M. Nolan

(57) ABSTRACT

The present invention provides a flowable material container closure assembly having a port tube and a membrane tube. The port tube (I) has a first layer and a second layer, (A) the first layer is a polymer blend and (B) the second layer is disposed coaxially within the first layer; and the membrane tube (II) is disposed coaxially within the port tube, the membrane tube has an outer layer, a core layer and an inner layer.

10 Claims, 1 Drawing Sheet

U.S. PATENT DOCUMENTS

| | | |
|---|---|---|
| 4,187,893 A | 2/1980 | Bujan .......................... 150/8 |
| 4,201,208 A | 5/1980 | Cambio, Jr. ............. 128/214.2 |
| 4,240,481 A | 12/1980 | Bayham ....................... 150/8 |
| 4,303,067 A | 12/1981 | Connolly et al. ........... 128/272 |
| 4,307,766 A | 12/1981 | Tanokura ...................... 150/8 |
| 4,327,726 A | 5/1982 | Kwong et al. ............. 128/272 |
| 4,340,049 A | 7/1982 | Munsch ................. 128/214 R |
| 4,362,158 A | 12/1982 | Lena ......................... 128/272 |
| 4,386,622 A | 6/1983 | Munsch ........................ 137/1 |
| 4,393,909 A | 7/1983 | Pearson ........................ 150/8 |
| 4,412,573 A | 11/1983 | Zdeb .......................... 604/415 |
| 4,441,538 A | 4/1984 | Larkin et al. ............... 604/145 |
| 4,465,488 A | 8/1984 | Richmond et al. .......... 604/414 |
| 4,479,989 A | 10/1984 | Mahal .......................... 428/35 |
| 4,484,916 A | 11/1984 | McPhee ..................... 604/256 |
| 4,516,977 A | 5/1985 | Herbert ...................... 604/415 |
| 4,523,691 A | 6/1985 | Larkin et al. ............... 220/266 |
| 4,524,880 A | 6/1985 | Danielson et al. .......... 220/288 |
| 4,547,900 A | 10/1985 | Larkin et al. .................. 383/5 |
| 4,551,138 A | 11/1985 | Shinohara ................... 604/262 |
| 4,567,999 A | 2/1986 | Hjertman et al. ............. 222/83 |
| 4,576,602 A | 3/1986 | Levin et al. ................ 604/408 |
| 4,578,074 A | 3/1986 | van Leerdam .............. 604/408 |
| 4,586,928 A | 5/1986 | Barnes et al. ............... 604/408 |
| 4,588,396 A | 5/1986 | Stroebel et al. ............. 604/246 |
| 4,588,777 A | 5/1986 | Hotta .......................... 525/93 |
| 4,596,573 A | 6/1986 | Donnan et al. ............. 604/415 |
| 4,607,671 A | 8/1986 | Aalto et al. ................. 141/329 |
| 4,610,374 A | 9/1986 | Buehler ....................... 222/83 |
| 4,632,673 A | 12/1986 | Tiitola et al. ............... 604/415 |
| 4,636,204 A | 1/1987 | Christopherson et al. ... 604/283 |
| 4,666,549 A | 5/1987 | Boultinghouse ......... 156/308.6 |
| 4,676,775 A | 6/1987 | Zolnierczyk et al. ......... 604/28 |
| 4,723,956 A | 2/1988 | Schnell et al. .............. 604/414 |
| 4,785,859 A | 11/1988 | Gustavsson et al. ........ 141/313 |
| 4,808,179 A | 2/1989 | Lindstam ................... 604/408 |
| 4,838,875 A | 6/1989 | Somor ....................... 604/262 |
| 4,857,129 A | 8/1989 | Jensen et al. .............. 156/273.7 |
| 4,869,384 A | 9/1989 | Ogle, II ...................... 215/247 |
| 4,917,684 A | 4/1990 | Yasumura ................... 604/468 |
| 4,950,347 A | 8/1990 | Futagawa ................. 156/272.4 |
| 4,969,883 A | 11/1990 | Gilbert et al. .............. 604/414 |
| 5,071,413 A | 12/1991 | Utterberg ................... 604/283 |
| 5,084,042 A | 1/1992 | McPhee ..................... 604/415 |
| 5,088,995 A | 2/1992 | Packard et al. ............. 604/415 |
| 5,114,768 A | 5/1992 | Swedberg ................ 428/36.91 |
| 5,122,126 A | 6/1992 | Sakakiyama ............... 604/415 |
| 5,125,919 A | 6/1992 | Miller et al. ................ 604/408 |
| 5,137,527 A | 8/1992 | Miller et al. ................ 604/415 |
| 5,167,816 A | 12/1992 | Kruger et al. ............ 210/257.2 |
| 5,188,628 A | 2/1993 | Rani et al. .................. 604/405 |
| 5,222,950 A | 6/1993 | Eisenberg ................... 604/408 |
| 5,251,982 A | 10/1993 | Stenstrom et al. .......... 383/209 |
| 5,259,843 A | 11/1993 | Watanabe et al. ........... 604/256 |
| 5,259,894 A | 11/1993 | Sampson ..................... 156/64 |
| 5,297,599 A | 3/1994 | Bucheli ...................... 141/329 |
| 5,303,751 A | 4/1994 | Slater et al. ................ 141/329 |
| 5,308,347 A | 5/1994 | Sunago et al. .............. 604/403 |
| 5,330,464 A | 7/1994 | Mathias et al. ............. 604/415 |
| 5,334,180 A | 8/1994 | Adolf et al. ................. 604/411 |
| 5,336,351 A | 8/1994 | Meyers ....................... 156/158 |
| 5,342,345 A | 8/1994 | Spencer ..................... 604/408 |
| 5,342,346 A | 8/1994 | Honda et al. ............... 604/413 |
| 5,352,210 A | 10/1994 | Marrucchi .................. 604/180 |
| 5,391,150 A | 2/1995 | Richmond .................. 604/111 |
| 5,395,365 A | 3/1995 | Weiler et al. ............... 604/415 |
| 5,416,142 A | 5/1995 | Bush et al. .................. 524/113 |
| 5,423,794 A | 6/1995 | Adolf et al. ................. 604/415 |
| 5,458,593 A | 10/1995 | Macabasco et al. ........ 604/403 |
| 5,514,123 A | 5/1996 | Adolf et al. ................. 604/411 |
| 5,520,641 A | 5/1996 | Behnke et al. ................ 604/86 |
| 5,529,821 A | 6/1996 | Ishikawa et al. ......... 428/36.91 |
| 5,540,674 A | 7/1996 | Karas et al. ................ 604/415 |
| 5,562,127 A | 10/1996 | Fanselow et al. ........... 138/137 |
| 5,573,527 A | 11/1996 | Macabasco et al. ........ 604/410 |
| 5,584,825 A | 12/1996 | Smith ........................ 604/319 |
| 5,601,889 A | 2/1997 | Chundury et al. ......... 428/34.3 |
| 5,662,642 A | 9/1997 | Isono et al. ................ 604/403 |
| 5,672,162 A | 9/1997 | Smith ........................ 604/319 |
| 5,728,087 A | 3/1998 | Niedospial, Jr. ............ 604/408 |
| 5,772,652 A | 6/1998 | Zielinski .................... 604/411 |
| 5,772,880 A | 6/1998 | Lynn et al. .................. 210/435 |
| 5,776,116 A | 7/1998 | Lopez et al. ................ 604/283 |
| 5,779,832 A | 7/1998 | Kocher ..................... 156/73.1 |
| 5,810,398 A | 9/1998 | Matkovich ...................... 285/3 |
| 5,814,384 A | 9/1998 | Akkapeddi et al. ........ 428/35.7 |
| 5,928,740 A | 7/1999 | Wilhoit et al. |
| 5,928,744 A | 7/1999 | Heilmann et al. .......... 428/36.3 |
| 5,998,019 A | 12/1999 | Rosenbaum et al. ........ 428/345 |
| 6,004,311 A | 12/1999 | Heilmann et al. ........... 604/319 |
| 6,004,636 A * | 12/1999 | Nicola et al. .............. 428/35.2 |
| 6,019,750 A | 2/2000 | Fowles et al. .............. 604/403 |
| 6,019,751 A | 2/2000 | Gabbard et al. ............ 604/408 |
| 6,022,344 A | 2/2000 | Meijer et al. ............... 604/533 |
| 6,083,194 A | 7/2000 | Lopez .......................... 604/28 |
| 6,127,009 A | 10/2000 | Strassmann ................ 428/35.2 |
| 6,132,413 A | 10/2000 | Mathias et al. ............. 604/403 |
| 6,146,362 A | 11/2000 | Turnbull et al. ............ 604/256 |
| 6,179,821 B1 | 1/2001 | Caspary et al. ............. 604/403 |
| 6,184,290 B1 * | 2/2001 | Ahmed et al. ................ 525/98 |

\* cited by examiner

PORT TUBE CLOSURE ASSEMBLY

TECHNICAL FIELD

The present invention relates generally to closures for flowable material containers and more particularly port tube assemblies for medical fluid containers.

BACKGROUND OF THE INVENTION

It is common medical practice to provide fluids to a patient either intravenously or enterally as a method of treating a patient for various medical conditions. Frequently, the fluids to be administered to a patient are contained in a flexible container. One method of forming a flexible container is to seal two sheets of flexible material about the periphery of the sheets to create a fluid tight chamber. A port tube assembly is frequently placed between the sheets during the sealing process to create a communication between the fluid chamber and the exterior of the container to provide a means of introducing fluid into or dispensing fluid from the container. The port tube assembly typically includes an outer port tube that attaches to the sidewalls of the container and a second tube called a membrane tube is disposed coaxially within the port tube. The membrane tube has a membrane or diaphragm that seals the port tube assembly. The membrane is typically punctured by a spike of a fluid administration set to place the contents of the container in fluid communication with a patient.

Port tubes and membrane tubes are fabricated from monolayer or multiple layered materials. The port tube typically has an inner layer of polyvinyl chloride and the membrane tube has an outer layer of PVC. To assemble the port tube assembly, the membrane tube is dipped in cyclohexanone or other suitable solvent and is inserted in a telescoping fashion into the port tube. The solvent melts the PVC of both the port tube and the membrane tube thereby hermetically sealing the membrane tube to the port tube.

There has been a great effort by many manufacturers of medical articles to replace PVC materials with non-PVC containing materials. Flexible PVC containers include low molecular weight additives know as plasticizers which may exude into the solutions contained in the container. U.S. Pat. Nos. 5,998,019 and 5,849,843, which are incorporated herein by reference and made a part hereof, disclose replacing PVC materials in medical fluid containers with non-PVC containing materials.

U.S. Pat. No. 5,356,709, assigned to the same assignee of the present invention, discloses a non-PVC coextruded medical grade port tubing. The tubing has an outer layer of a blend of polypropylene and SEBS a tie layer and a core layer of a blend of polyamide and EVA.

U.S. Pat. No. 5,533,992, assigned to the same assignee of the present invention, discloses a non-PVC material for fabricating medical tubings and medical containers. Polymer blends for fabricating medical tubing disclosed in the '992 Patent include polyurethane blended with one or more of the following: EVA, SEBS, PCCE, thermoplastic copolyester elastomers.

SUMMARY OF THE INVENTION

The present invention provides a non-PVC port tube, a non-PVC membrane tube and a non-PVC port tube assembly for use in flowable material containers such as medical and food containers.

The closure assembly includes a port tube and a membrane tube coaxially mounted therein. The port tube has a first layer and a second layer. The first layer is a multiple component polymer blend having a first component in an amount by weight of from about 25% to about 50% by weight of the first layer. The first component is a first polyolefin selected from the group consisting of polypropylene and polypropylene copolymers. The second component is present in an amount by weight of from about 0% to about 50% by weight of the first layer and is a second polyolefin. The second polyolefin is selected from the group consisting of ethylene copolymers, ultra-low density polyethylene, polybutene, polybutadiene and butene ethylene copolymers. The third component is present in an amount by weight of from about 0% to about 40% by weight of the first layer and is a radio frequency ("RF") susceptible polymer. The RF polymer is selected from the group consisting of polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12%–50% by weight of the copolymer, ethylene methyl acrylate copolymers with methyl acrylate comonomer content from 12%–40% by weight of the copolymer, ethylene vinyl alcohol with vinyl alcohol comonomer content from 12%–70% by mole percent of the copolymer. The fourth component is present in an amount from about 0% to about 40% and is a first thermoplastic elastomer.

The second layer of the port tube is disposed coaxially within the first layer and in a preferred form of the invention is a polymeric material that is susceptible of solvent bonding and more preferably includes a second thermoplastic elastomer. Optionally, the second layer can include an additive from about 0% to about 20% by weight of a polypropylene, high density polyethylene, silica, slip agents, fatty amides, acrawax and the like.

The membrane tube has an outer layer, a core layer and an inner layer. The outer layer of the membrane tube is capable of being solvent bonded to the second layer of the port tube. In a preferred form of the invention, the outer layer of the membrane tube (A) is a polymer blend of. (1) from about 0% to about 60% by weight of the outer layer of a third polyolefin and (2) from about 40% to about 100% by weight of the outer layer of a second component of a third thermoplastic elastomer. The core layer (B) is attached to the outer layer. In a preferred form of the invention, the core layer is a polymer blend of: (1) from about 35% to about 100% by weight of the core layer of a fourth thermoplastic elastomer and (2) from about 0% to about 65% by weight of the core layer of a fourth polyolefin.

The inner layer of the membrane tube is attached to the core layer on a side opposite of the outer layer. The inner layer is a multiple component polymer blend of and in a preferred form has: (1) from about 25% to about 55% by weight of the inner layer a fifth polyolefin, (2) from about 0% to about 50% by weight of the inner layer a sixth polyolefin selected from the group consisting of ethylene copolymers, ultra-low density polyethylene, polybutene, and butene ethylene copolymers; (3) from about 0% to about 40% by weight of the inner layer of a radio frequency susceptible polymer selected from the group consisting of polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12%–50% by weight of the copolymer, ethylene methyl acrylate copolymers with methyl acrylate comonomer content from 12%–40% by weight of the copolymer, ethylene vinyl alcohol with vinyl alcohol comonomer content from 12%–70% by mole percent of the copolymer; and (4) from about 0% to about 40% by weight of the inner layer of a fifth thermoplastic elastomer.

DETAILED DESCRIPTION

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

Figure 1:
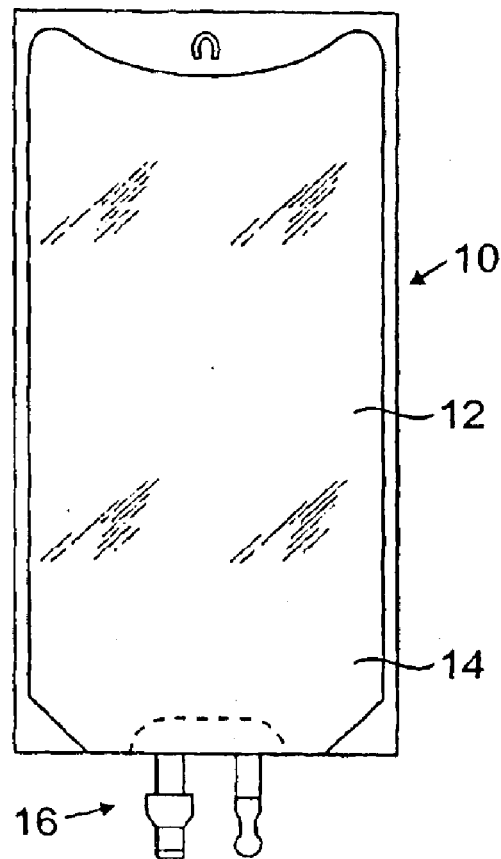
FIG. 1 is a plan view of a flowable material container with port closure assembly.

FIG. 1 shows a flowable material container 10 having sidewalls 12 sealed along peripheral edges to define a chamber 14 therebetween. A port tube closure assembly 16 provides access to the contents of the container. The container 10 is preferably fabricated from a non-PVC containing material. In a preferred form of the invention the sidewalls 12 are fabricated from a multiple component polymer alloy such as those disclosed in detail in U.S. Pat. No. 5,686,527 which is incorporated herein by reference and made a part hereof. One particularly suitable polymer alloy is a blend of polypropylene, ultra-low density polyethylene, a polyamide and a styrene and hydrocarbon block copolymer. The container 10 shown in FIG. 1 is particularly suitable for medical applications such as storage and delivery of I.V. solutions, peritoneal dialysis solutions, pharmaceutical drugs and blood and blood components to name a few. It is contemplated that such a container can also be used to store food products, serve as a drain bag for peritoneal dialysis or store other consumable products.

What is meant by "flowable material" is a material that will flow by the force of gravity. Flowable materials therefore include both liquid items and powdered or granular items and the like.

Figure 2:
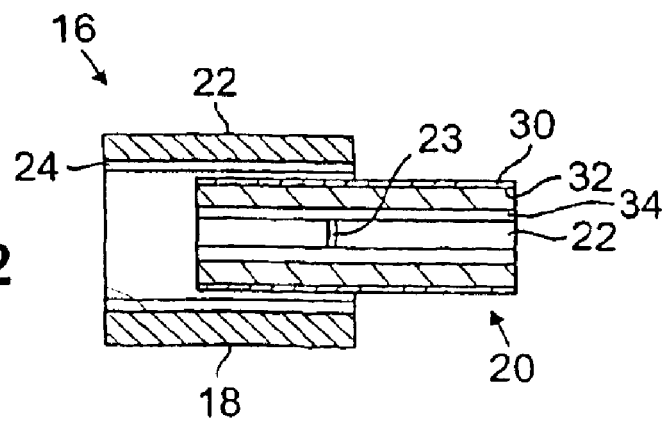
FIG. 2 is a cross-sectional view of a port tube of the present invention.

FIG. 2 shows the port tube assembly 16. The port tube assembly 16 has a port tube 18 and a membrane tube 20 coaxially mounted therein. A fluid passageway 22 of the membrane tube 20 is sealed by a membrane 23 positioned at an intermediate portion of the membrane tube 20. For medical applications, the membrane 23 can be punctured by a spike of an infusion set to place the contents of the container into fluid communication with, for example, the vascular system of a patient being treated.

In a preferred form of the invention the port tube 18 is a multilayered structure and more preferably has a first layer 22 and a second layer 24. The first layer 22 should be of a non-PVC containing material that is capable of being sealed to the sidewalls 12 of the container 10, and preferably sealed using radio frequency sealing techniques. In a preferred form of the invention the first layer 22 is a polymer blend of: (a) from about 25% to about 50%, more preferably from about 30% to about 40%, by weight of the first layer a first polyolefin selected from the group consisting of polypropylene and polypropylene copolymers, (b) from about 0% to about 50%, more preferably from about 5% to about 40%, by weight of the first layer a second polyolefin of an α-olefin containing polymer or copolymer and more preferably is an ethylene and α-olefin copolymer; (c) from about 0% to about 40%, more preferably from about 10% to about 40% of the first layer a radio frequency susceptible polymer selected from the group consisting of polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12%–50% by weight of the copolymer, ethylene methyl acrylate copolymers with methyl acrylate comonomer content from 12%–40% by weight of the copolymer, ethylene vinyl alcohol with vinyl alcohol comonomer content from 12%–70% by mole percent of the copolymer; and (d) from about 0% to about 40%, more preferably from about 10% to about 40% of a thermoplastic elastomer by weight of the first layer.

The second layer 24 of the port tube 18 is of a non-PVC containing material that is capable of being solvent bonded to the membrane tube 20. In a preferred form of the invention the second layer 24 is a thermoplastic elastomer or a blend of a thermoplastic elastomer in an amount by weight of from about 80% to about 100% and a propylene containing polymer from about 0% to about 20% by weight of the second layer 24. It is also desirable, but optional, that the second layer 24 softens slightly at autoclave temperatures so that when the port tube and membrane tube assembly is steam sterilized, the port tube more tightly adheres to the membrane tube.

As shown in the Figures, the first layer has a thickness greater than the second layer. In a preferred form of the invention the first layer will have a thickness of from about 15 mils to about 40 mils and more preferably from about 20 mils to about 30 mils. The second layer will have a thickness from about 2 mils to about 10 mils and more preferably from about 3 mils to about 7 mils.

The membrane tube 20 should be fabricated from a non-PVC containing material and should be capable of being bonded to the port tube 18, preferably using solvent bonding techniques. Solvent bonding is well known in the art. Solvent bonding typically includes applying a solvent to a polymeric material to partially dissolve the polymer. While in this dissolved state the dissolved polymer material is placed in contact with a material, such as another polymer, that the polymeric material is to be bonded to. Suitable solvents for solvent bonding of the materials of the present invention include at least the following aromatic solvents: cyclohexane, cyclohexanone, toluene, tetrahydofuran, cumene, xylenes, diethyl benzene, decalin, tetralin and amyl benzene to name a few.

Accordingly, to solvent bond the membrane tube to the port tube, a portion of the membrane tube that is to be in contact with the port tube is exposed to the solvent, typically by dipping the relevant portion of the membrane tube into the solvent. Then the membrane tube is inserted into the membrane tube in telescoping fashion where a strong bond is formed.

In a preferred form of the invention the membrane tube 20 is a multilayered structure having an outer layer 30, a core layer 32 and an inner layer 34. In a preferred form of the invention the outer layer 30 is a polymer blend of: (a) from about 0% to about 60%, more preferably from about 20% to about 55% and most preferably from about 30% to about 50%, by weight of the outer layer of a polyolefin and (b) from about 40% to about 100%, more preferably from about 45% to about 80% and most preferably from about 50% to about 70%, by weight of the outer layer of a thermoplastic elastomer.

Also, in a preferred form of the invention the core layer 32 is a polymer blend of: (a) from about 35% to about 100%, more preferably from about 50% to about 90% and most preferably 70% to about 90%, by weight of the core layer of a thermoplastic elastomer and (b) from about 0% to about 65%, more preferably from about 10% to about 50% and most preferably from about 10% to about 30%, by weight of the core layer of a polyolefin.

Also, in a preferred form of the invention, the inner layer 34 is a polymer blend of: (a) from about 25% to about 55%, more preferably from about 25% to about 40%, by weight of the inner layer a polyolefin; (b) from about 0% to about 50%, more preferably from about 0% to about 40% and most preferably 0% to about 20%, by weight of the inner layer a polyolefin selected from the group consisting of α-olefin containing polymers or copolymers and more preferably is an ethylene and α-olefin copolymer; (c) from about 0% to about 40% by weight, more preferably from about 15% to about 40%, of the inner layer a radio frequency susceptible polymer selected from the group consisting of polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12%–50% by weight of the copolymer, ethylene methyl acrylate copolymers with methyl acrylate comonomer content from 12%–40% by weight of the copolymer, ethylene vinyl alcohol with vinyl alcohol comonomer content from 12%–70% by mole percent of the copolymer; and (d) from about 0% to about 40%, more preferably from about 15% to about 40%, by weight of the inner layer of a thermoplastic elastomer.

In a preferred form of the invention the outer layer 30 will have a thickness from about 3 mils to about 15 mils and more preferably from about 3 mils to about 10 mils. The core layer 32 will have a thickness from about 10 mils to about 35 mils and more preferably from about 10 mils to about 30 mils. The inner layer 34 will have a thickness from about 3 mils to about 15 mils and more preferably from about 5 mils to about 10 mils.

Thermoplastic elastomers include styrene and hydrocarbon copolymers, EPDM, and ethylene propylene rubber. The styrene can be substituted or unsubstituted styrene. The styrene and hydrocarbon copolymers can be block copolymer including di-block, tri-block, star block, it can also be a random copolymer and other types of styrene and hydrocarbon copolymers that are known by those skilled in the art. Styrene and hydrocarbon copolymers therefore include for example, but are not limited to, styrene-butene-styrene block copolymer, styrene-ethylene-butene-styrene block copolymers, styrene-isobutene-styrene and the numerous other varieties of styrene and hydrocarbon copolymers that are well known in the art. The styrene and hydrocarbon copolymers can also be blends of various types of the above-identified styrene and hydrocarbon copolymers.

The styrene and hydrocarbon copolymers can be modified or functionalized by carboxylic acid groups, anhydrides of carboxylic acids, esters of carboxylic acids, epoxy groups and carbon monoxide. In a preferred form of the invention the thermoplastic elastomer of the first layer 22 of the port tube 18 and the inner layer 34 of the membrane tube 20 is an SEBS copolymer with a maleic anhydride group in an amount by weight of about 2% or less. Such a copolymer is sold by Shell Chemical Company under the tradename KRATON® FG1924X and FG1901X.

The thermoplastic elastomer of the second layer 24 of the port tube 18 and the outer layer 30 of the membrane tube 20 is preferably a styrene and diene copolymer more preferably selected from the group consisting of styrene-ethylene-butene-styrene copolymers, and styrene-isoprene-styrene copolymers. More preferably the thermoplastic elastomer of the second layer is an ethylene butene copolymer, and more preferably a styrene-ethylene-butene-styrene copolymer. It has been found that such a copolymer is well suited for solvent bonding. Suitable SEBS copolymers are sold by Shell Chemical Company under the tradename KRATON® KG1657.

The thermoplastic elastomer of the core layer of the membrane tube is an SEBS copolymer containing a high proportion of triblock. Suitable polymers are sold by Shell Chemical Company under the tradename KRATON® KG1660, KG1652 and KG1650.

Suitable polypropylene polymers include homopolymers and copolymers. Suitable comonomers are α-olefin s having from 2 to 17 carbons and most preferably is ethylene in an amount by weight from about 1 to about 8% by weight of the copolymer.

Suitable α-olefin containing polymers include homopolymers, copolymers and interpolymers of α-olefins having from 2 to 17 carbons. Suitable ethylene α-olefin copolymers of the first layer 22 of the port tube 18 and the inner layer 34 of the membrane tube 20 have a density, as measured by ASTM D-792, of less than about 0.915 g/cc, more preferably less than about 0.905 g/cc, and are commonly referred to as very low density polyethylene (VLDPE), ultra low density polyethylene (ULDPE) and the like. In a preferred form of the invention, the ethylene and α-olefin copolymers are obtained using a single site catalyst such as metallocene catalysts, vanadium catalysts and the like. Suitable catalyst systems, among others, are those disclosed in U.S. Pat. Nos. 5,783,638 and 5,272,236. Suitable ethylene and α-olefin copolymers include those sold by Dow Chemical Company under the AFFINITY tradename, Dupont-Dow under the ENGAGE tradename, Exxon under the EXACT tradename and Phillips Chemical Company under the tradename MARLEX.

The port tube assembly, in a preferred form of the invention satisfies the following physical properties: (1) has a spike insertion force of less than about 35 lbs on average, (2) has a spike removal force of greater than about 5 lbs on average. The pull force to separate the membrane tube from the port tube is greater than the spike removal force.

The following is a non-limiting example of the present invention.

EXAMPLES

A two layered port tube having an outer and an inner layer was coextruded. The inner layer had a thickness of 0.006 inches and was fabricated from SEBS. The outer layer had a thickness of 0.026 inches and was fabricated from a polymer blend by weight of the outer layer of 35% polypropylene/5% ultra low density polyethylene/30% dimer fatty acid polyamide/30% SEBS with maleic anhydride functionality.

A three layered membrane tube was coextruded having an inner layer, a core layer and an outer layer. The inner layer is a polymer blend by weight 30% polypropylene/35% dimer fatty acid polyamide/35% SEBS. The core layer was a blend of 85% SEBS and 15% polypropylene. The outer layer was 45% SEBS and 55% polypropylene. The inner layer had a thickness of 0.003 inches, the core layer 0.023 inches and the outer layer 0.006 inches.

Polymeric sheeting was extruded from a blend by weight of 10% dimer fatty acid polyamide, 35% ultra low density polyethylene, 45% polypropylene and 10% SEBS with maleic anhydride functionality.

Two rectangularly-shaped sheets of the polymeric sheeting were placed into registration and sealed along 3 peripheral edges to define a pouch. A port tube segment was inserted into an open end of the pouch and was heat sealed therein while sealing the final peripheral edge to define a container. A membrane tube segment was dipped into cyclohexanone and inserted in a telescoping fashion into the port tube segment.

The container was bolted down proximate a mechanical tester. The port tube was attached to a spike attached to a cross-head of the mechanical tester. The cross-head speed of the tester was set at 20 in/min. The cross-head was set to achieve the desired spike insertion depth in the port tube. The tester allowed for measuring the spike insertion force and the spike removal force. The average spike insertion value after 50 tests was 13.31 lbf. The average spike removal force for 50 tests was 10.37 lbf. These measurements were made after the spike dwelled in the membrane tube for 24 hours.

The tester was also used to determine the pull force necessary to remove the port tube from the container or to otherwise damage the container or port tube. The port tube was inserted into the tester with the container bolted down. The average pull force for 28 tests was 30.04 lbf. This test was conducted prior to steam sterilizing the container. The value for 30 test after the container was steam sterilized was 42.68 lbf.

We claim:

1. A multiple layered non-PVC containing tubing comprising:
    a first layer of a polymer blend composed of: (a) from about 25% to about 50% by weight of the first layer of a first polyolefin selected from the group consisting of polypropylene and polypropylene copolymers, (b) from about 1 to about 50% by weight of the first layer of a second polyolefin selected from the group consisting of ethylene copolymers, ultra-low density polyethylene, polybutene, polybutadiene and butene ethylene copolymers; (c) from about 1% to about 40% by weight of the first layer of a radio frequency susceptible polymer selected from the group consisting of polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12%–50% by weight of the copolymer, ethylene methyl acrylate copolymers with methyl acrylate comonomer content from 12%–40% by weight of the copolymer, ethylene vinyl alcohol copolymer with vinyl alcohol comonomer content from 12%–70% by mole percent of the copolymer; (d) from about 1% to about 40% of a first thermoplastic elastomer; and
    a second layer disposed coaxially within the first layer and being a second thermoplastic elastomer composed solely of a styrene and diene copolymer.

2. The tubing of claim 1 wherein the polyamide is selected from a group consisting of aliphatic polyamides resulting from the condensation reaction of diamines having a carbon number within a range of 2–13, aliphatic polyamides resulting from a condensation reaction of di-acids having a carbon number within a range of 2–13, polyamides resulting from the condensation reaction of dimer fatty acids, and amide containing copolymers.

3. The tubing of claim 1 wherein the polyamide is a dimer fatty acid polyamide.

4. The tubing of claim 1 wherein the first polyolefin is a propylene copolymerized with a monomer selected from the group consisting of α-olefin s having from 2–17 carbons.

5. The tubing of claim 4 wherein the first polyolefin is a propylene and ethylene copolymer having an ethylene content of from about 1% to about 8% by weight of the first polyolefin.

6. The tubing of claim 1 wherein the second thermoplastic elastomer has a polymer structure selected from the group consisting of diblock, triblock, radial block, and star block.

7. The tubing of claim 6 wherein the second thermoplastic elastomer is selected from the group consisting of styrene-ethylene-butene-styrene copolymers and styrene-isoprene-styrene copolymers.

8. The tubing of claim 7 wherein the second thermoplastic elastomer contains styrene-ethylene-butene-styrene diblock copolymer and a styrene-ethylene-butene-styrene triblock copolymer.

9. The tubing of claim 1 wherein the second polyolefin is an ethylene copolymerized with a monomer selected from the group consisting of α-olefins.

10. The tubing of claim 9 wherein the ethylene and α-olefin copolymer is obtained using a single-site catalyst.

* * * * *